US012590280B2

(12) United States Patent
Kondo et al.

(10) Patent No.: US 12,590,280 B2
(45) Date of Patent: Mar. 31, 2026

(54) FILTRATION AND COLLECTION DEVICE

(71) Applicant: Murata Manufacturing Co., Ltd.,
Nagaokakyo (JP)

(72) Inventors: Takashi Kondo, Nagaokakyo (JP);
Shogo Tokoi, Nagaokakyo (JP)

(73) Assignee: **MURATA MANUFACTURING CO.,
LTD.**, Nagaokakyo (JP)

( * ) Notice: Subject to any disclaimer, the term of this
patent is extended or adjusted under 35
U.S.C. 154(b) by 1025 days.

(21) Appl. No.: 17/666,795

(22) Filed: Feb. 8, 2022

(65) Prior Publication Data

US 2022/0162539 A1 May 26, 2022

Related U.S. Application Data

(63) Continuation of application No.
PCT/JP2020/030594, filed on Aug. 11, 2020.

(30) Foreign Application Priority Data

Sep. 17, 2019 (JP) ................................. 2019-168535

(51) Int. Cl.
*C12M 1/00* (2006.01)
*C12M 1/12* (2006.01)
(52) U.S. Cl.
CPC ............ *C12M 29/04* (2013.01); *C12M 23/06*
(2013.01)
(58) Field of Classification Search
None
See application file for complete search history.

(56) References Cited

U.S. PATENT DOCUMENTS

2013/0306576 A1 11/2013 Bosio et al.
2019/0118125 A1 4/2019 Banju et al.

FOREIGN PATENT DOCUMENTS

| CN | 204891342 U | 12/2015 |
|---|---|---|
| CN | 207221975 U | 4/2018 |
| JP | S52160880 U | 12/1977 |
| JP | S56172330 U | 12/1981 |
| JP | H02125727 U | 10/1990 |
| JP | 2013141456 A | 7/2013 |
| JP | 2013236631 A | 11/2013 |

(Continued)

OTHER PUBLICATIONS

Document entitled WO2017/191768A1 Filtration Filter Device,
machine translation of WO 2017/191768 A1 provided by Espacenet,
original document published 1027. (Year: 2017).*

(Continued)

*Primary Examiner* — Michael A Marcheschi
*Assistant Examiner* — Ashley Lopezlira
(74) *Attorney, Agent, or Firm* — ArentFox Schiff LLP

(57) ABSTRACT

A filtration and collection device capable of improving the
collection rate of filtration targets. The filtration and collec-
tion device may include a holder having an inlet port for
pouring a liquid, a discharge port for discharging the liquid,
a flow path through which the inlet port and the discharge
port communicate, and a groove portion formed on an outer
periphery of the holder, a filter disposed in the flow path of
the holder and having a plurality of through-holes, and one
or a plurality of grip sections having an insertion portion that
is inserted into the groove portion, in which a gap is formed
between the groove portion and the insertion portion.

20 Claims, 16 Drawing Sheets

(56)     References Cited

FOREIGN PATENT DOCUMENTS

| WO | WO-2017022419 | A1 | * | 2/2017 | ............ B01D 39/12 |
|----|----|----|----|----|----|
| WO | WO-2017022484 | A1 | * | 2/2017 | ............ B01D 29/01 |
| WO | WO-2017191768 | A1 | * | 11/2017 | ............ B01D 29/05 |
| WO | WO-2018030061 | A1 | * | 2/2018 | ............ B01D 29/05 |

OTHER PUBLICATIONS

Document entitled WO2018/030061A1 Filtration Filter Device,
machine translation of WO 2018/030061 A1 provided by Espacenet,
original document published 2018. (Year: 2018).*
International Search Report in PCT/JP2020/030594, mailed Oct. 20,
2020, 3 pages.

* cited by examiner

| | | CELL IN LIQUID DISCHARGED INTO CENTRIFUGE TUBE | CELL CAPTURED BY FILTER |
|---|---|---|---|
| EXAMPLE 1 | CELL AGGREGATION | 0 | 2 |
| | SINGLE CELL | 14 | 1 |
| COMPARATIVE EXAMPLE 1 | CELL AGGREGATION | 0 | 1 |
| | SINGLE CELL | 5 | 12 |

FILTRATION AND COLLECTION DEVICE

CROSS REFERENCE TO RELATED APPLICATIONS

This application is a continuation of International Application No. PCT/JP2020/030594, filed Aug. 11, 2020, which claims priority to Japanese Patent Application No. 2019-168535, filed Sep. 17, 2019, the entire contents of each of which are hereby incorporated in their entirety.

TECHNICAL FIELD

The present disclosure is directed to a filtration and collection device.

BACKGROUND OF THE INVENTION

Japanese Unexamined Patent Application Publication No. 2013-141456 (hereinafter "JP '456") describes, for example, a device for filtering a liquid containing filtration targets, more specifically, a cell strainer. The cell strainer as described in JP '456, has a filtering portion (filter) that opens upward to filter a liquid, a holding portion that holds the filter portion inside an opening portion of a tube, and a communication portion through which the inside and the outside of the tube communicate when the cell strainer is held in the tube. The cell strainer as described in JP '456, has the filter portion disposed on the side surface and the bottom surface of the holding portion.

However, the cell strainer as described in JP '456 does not meet the collection rate of the filtration targets.

SUMMARY OF THE INVENTION

According to an exemplary aspect of the disclosure, the device provides a filtration and collection device capable of improving the collection rate of filtration targets.

A filtration and collection device according to one aspect of the present disclosure includes a holder having an inlet port for pouring a liquid, a discharge port for discharging the liquid, a flow path through which the inlet port and the discharge port communicate, and a groove portion formed on an outer periphery of the holder, a filter disposed in the flow path of the holder and having a plurality of through-holes, and one or a plurality of grip sections having an insertion portion that is inserted into the groove portion, in which a gap is formed between the groove portion and the insertion portion.

According to the present disclosure, it is possible to provide a filtration and collection device capable of improving the collection rate of filtration targets.

Additional advantages and novel features of the system of the present disclosure will be set forth in part in the description that follows, and in part will become more apparent to those skilled in the art upon examination of the following or upon learning by practice of the disclosure.

BRIEF DESCRIPTION OF THE DRAWINGS

In the descriptions that follow, like parts are marked throughout the specification and drawings with the same numerals, respectively. The drawings are not necessarily drawn to scale and certain drawings may be shown in exaggerated or generalized form in the interest of clarity and conciseness. The disclosure itself, however, as well as a mode of use, further features and advances thereof, will be understood by reference to the following detailed description of illustrative implementations of the disclosure when read in conjunction with reference to the accompanying drawings, wherein.

DETAILED DESCRIPTION

Figure 1:
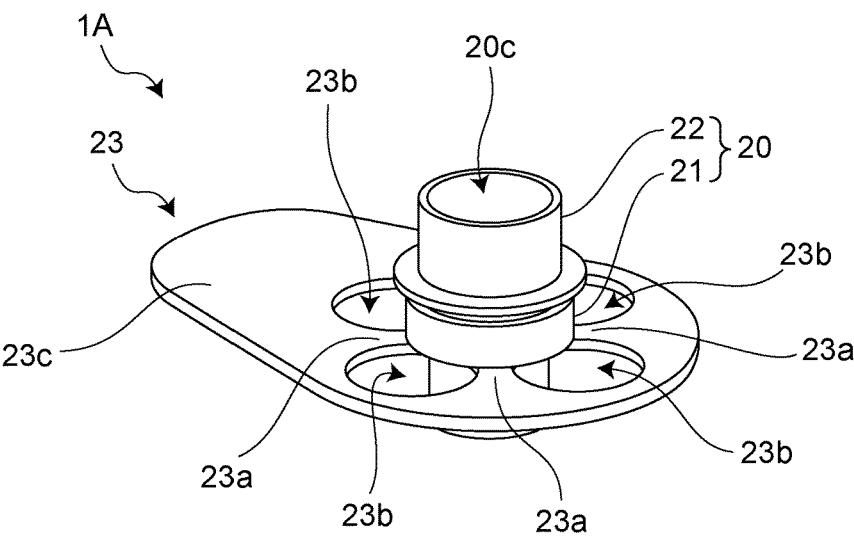
FIG. 1 is a schematic perspective view of an example of a filtration and collection device in accordance with aspects of the present disclosure.
Figure 1:
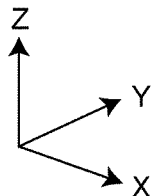

A liquid containing filtration targets may be passed through a cell strainer to separate the filtration targets by size. In this case, the filtration targets are separated into smaller targets passing through through-holes of the cell strainer and targets larger than the through-holes of the filter. After pouring the liquid into the cell strainer for separation of the filtration targets, small filtration targets that should pass through the through-holes of the cell strainer may remain attached to the cell strainer.

As a result, there is a problem in that the collection rate of the filtration targets is lowered. In addition, when the cell strainer is connected to a liquid storage container in use, the pressure inside the container increases, and the liquid does not easily pass through the cell strainer. Therefore, there may be a problem that the processing time of the liquid becomes long and the processing efficiency decreases.

Further, by stacking cell strainers having different through-hole sizes, filtration targets of different sizes may be simultaneously separated. In the cell strainer described above, the filter portion and the grip portion are integrally formed, and when the cell strainer is connected to the liquid storage container in use, it is difficult to stack and use the plurality of cell strainers due to the interference of the grip portions. In addition, when the plurality of liquid storage containers to which the plurality of cell strainers are connected are simultaneously used on a flat plane, since the grip portions interfere with each other, a certain arrangement distance is required between the liquid storage containers. Therefore, it is difficult to simultaneously use the plurality of cell strainers on a limited work plane. Further, when the filter portion and the grip portion are integrally formed, the grip portion may be mistakenly touched when observing the filter portion under a microscope, and as a result, the observation area may shift.

Therefore, in accordance with an aspect of the disclosure, a filter portion and a grip portion are separate components.

A filtration and collection device according to one aspect of the present disclosure includes a holder having an inlet port for pouring a liquid, a discharge port for discharging the liquid, a flow path through which the inlet port and the discharge port communicate, and a groove portion formed on an outer periphery of the holder, a filter disposed in the flow path of the holder and having a plurality of through-holes, and one or a plurality of grip sections having an insertion portion that is inserted into the groove portion, in which a gap is formed between the groove portion and the insertion portion.

With such a configuration, is may be possible to improve a collection rate of the filtration targets.

In the filtration and collection device described below, the holder may include a first holder having a tubular shape and the groove portion and a second holder to be fitted into the first holder, and the filter may be held by the first holder and the second holder.

With such a configuration, the filter can be detached from the holder.

In the filtration and collection device, the insertion portion may be formed with one or a plurality of notch portions.

With such a configuration, ventilation is possible between the inside and the outside of the liquid storage container, and the liquid permeability of the filter can be improved.

In the filtration and collection device as described below, the plurality of notch portions may be provided at equal distances.

With such a configuration, insertion portions are inserted into the groove portion at equal distances, so that the stability of the grip section to the holder is improved.

In the filtration and collection device as described below, the holder may have a cylindrical shape, and the plurality of grip sections may be formed in a flat plate shape and may be stacked in a thickness direction.

With such a configuration, one of the grip sections can be rotated to change the size of the hole formed by the plurality notch portions, and the flow rate can be adjusted.

In the filtration and collection device, the grip section may be formed in a flat plate shape and have a principal surface, and one or a plurality of convex portions may be formed on the principal surface.

With such a configuration, a vent hole may be formed between the grip section and the liquid storage container, so that the liquid permeability can be improved.

Hereinafter, one aspect of the disclosure will be described with reference to the accompanying drawings. Note that, in the drawings, elements are exaggeratedly illustrated in order to facilitate the description.

The filtration and collection device according to one aspect of the disclosure is a device capable of performing filtration and collection. Specifically, the filtration and collection device filters a liquid containing filtration targets through a filter and collects filtration targets having passed through the filter or filtration targets captured by the filter.

In the specification, the term "filtration targets" means targets that should be separated by filtration among targets contained in the liquid. For example, the filtration targets may be biological substances contained in the liquid. The term "biological substance" means a substance derived from an organism such as a cell (eukaryotic cell), a bacterium (eubacterium), and a virus. Examples of cells (eukaryotes) include, for example, induced pluripotent stem cells (iPS cells), ES cells, stem cells, mesenchymal stem cells, mononuclear cells, unicellular cells, cell aggregations, floating cells, adherent cells, nerve cells, white blood cells, regenerative medical cells, autologous cells, cancer cells, blood circulating tumor cells (CTC), HL-60, HELA, and fungi. Examples of bacteria (eubacteria) include, for example, *Escherichia coli* and *Mycobacterium tuberculosis*.

In an exemplary aspect, the liquid will be described as a cell suspension and the filtration targets will be described as cells.

Figure 2:
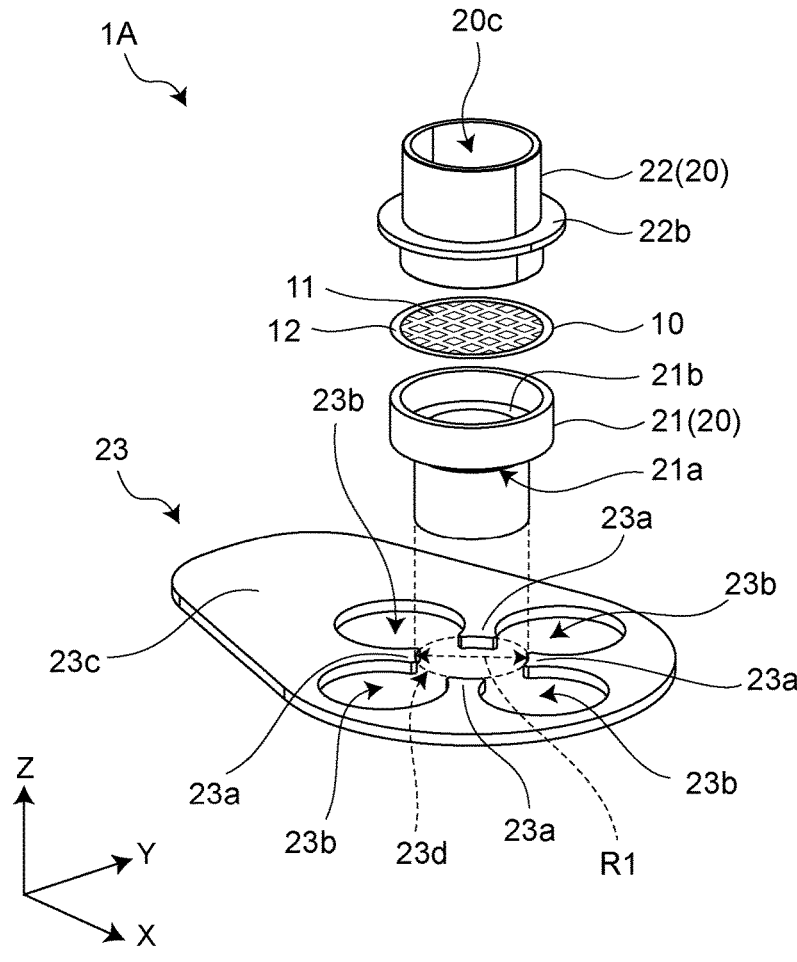
FIG. 2 is a schematic exploded perspective view of the example of the filtration and collection device in accordance with aspects of the present disclosure.
Figure 3:
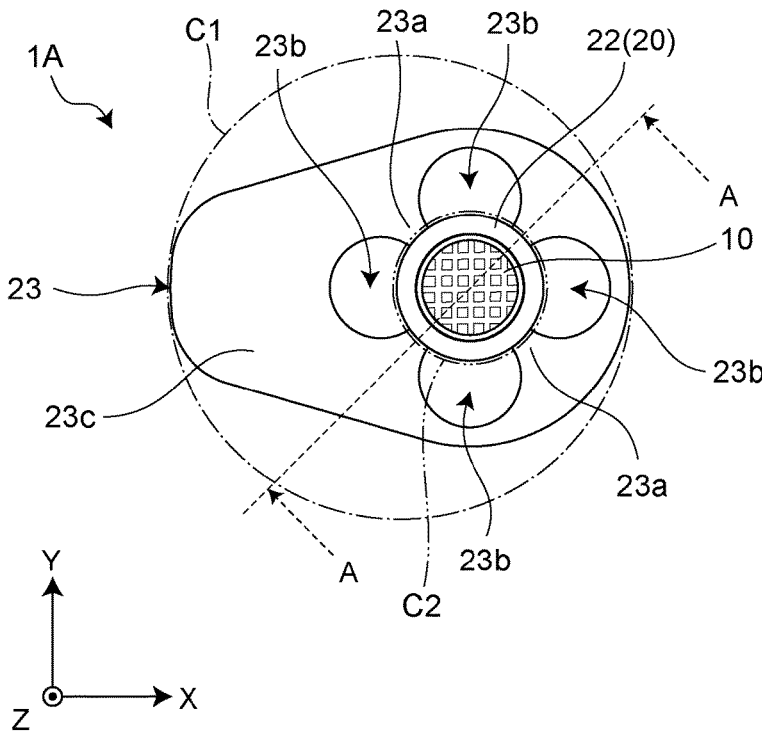
FIG. 3 is a schematic plan view of the example of the filtration and collection device in accordance with aspects of the present disclosure.
Figure 4A:
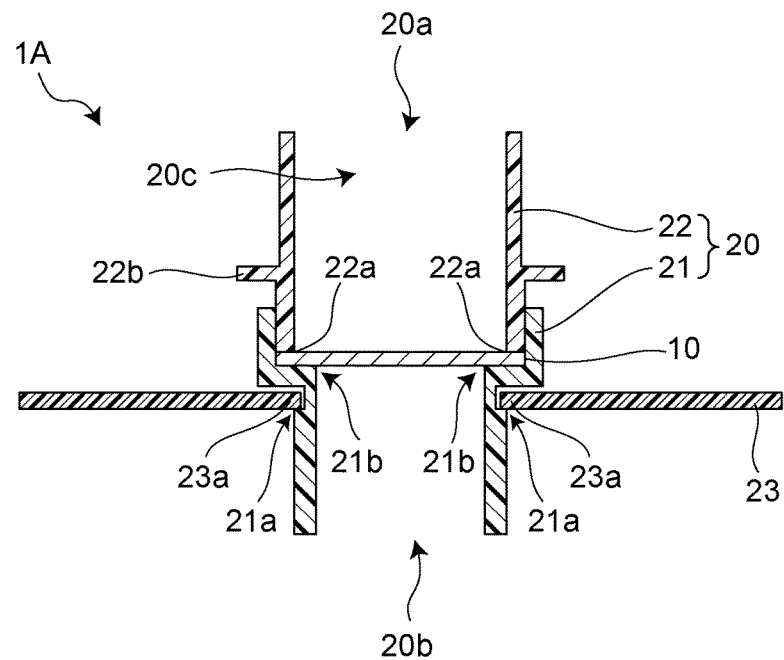
FIG. 4A is a sectional view taken along line A-A of the filtration and collection device of FIG. 3.
Figure 4B:
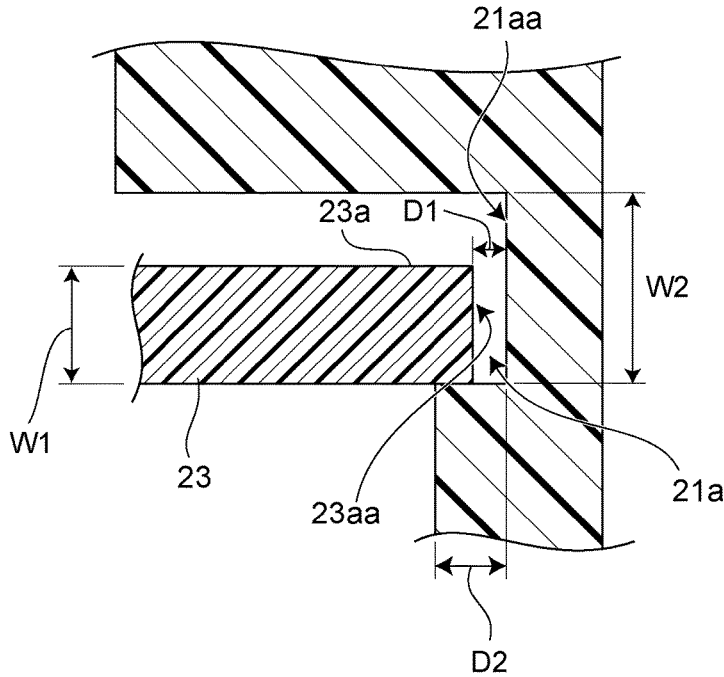
FIG. 4B is an enlarged view of a part of the filtration and collection device of FIG. 4A.

FIG. 1 is a schematic perspective view of an example of a filtration and collection device 1A according to one aspect of the disclosure. FIG. 2 is a schematic exploded perspective view of the example of the filtration and collection device 1A according to one aspect of the present disclosure. FIG. 3 is a schematic plan view of the example of the filtration and collection device 1A according to one aspect of the present disclosure. FIG. 4A is a sectional view taken along line A-A of the filtration and collection device 1A of FIG. 3. FIG. 4B is an enlarged view of a part of the filtration and collection device 1A of FIG. 4A. X, Y, and Z directions in FIGS. 1 to 3 indicate a longitudinal direction, a lateral direction, and a thickness direction of the filtration and collection device 1A, respectively.

As illustrated in FIGS. 1 to 4B, the filtration and collection device 1A includes a filter 10, a holder 20 that holds the filter 10, and a grip section 23 attached to the holder 20.

The filter 10 is a metal filter. Specifically, the filter 10 contains, as a main component, at least one of a metal and a metal oxide. The filter 10 includes a filter portion 11 having a plurality of through-holes and a frame portion 12 disposed so as to surround an outer periphery of the filter portion 11. In accordance with an aspect of the disclosure, the filter portion 11 and the frame portion 12 are integrally formed.

Figure 5:
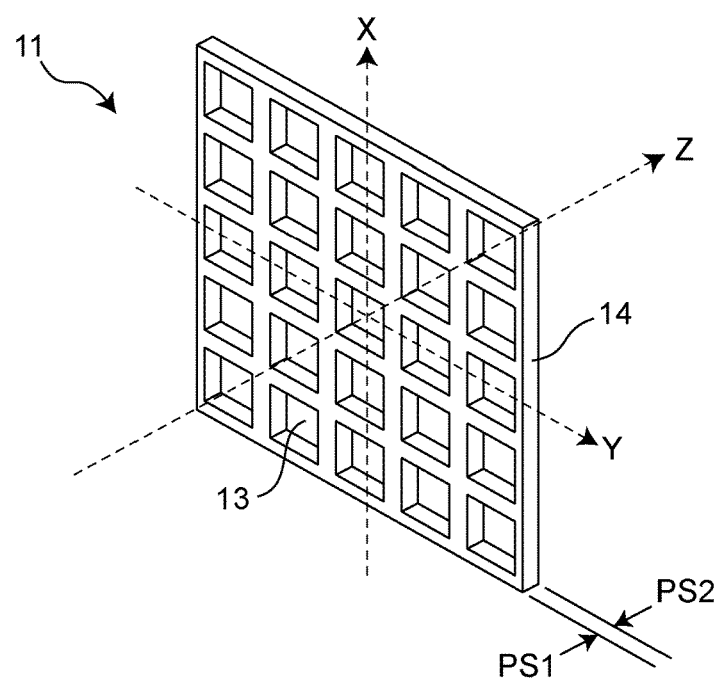
FIG. 5 is an enlarged perspective view of a part of an example of a filter portion.
Figure 6:
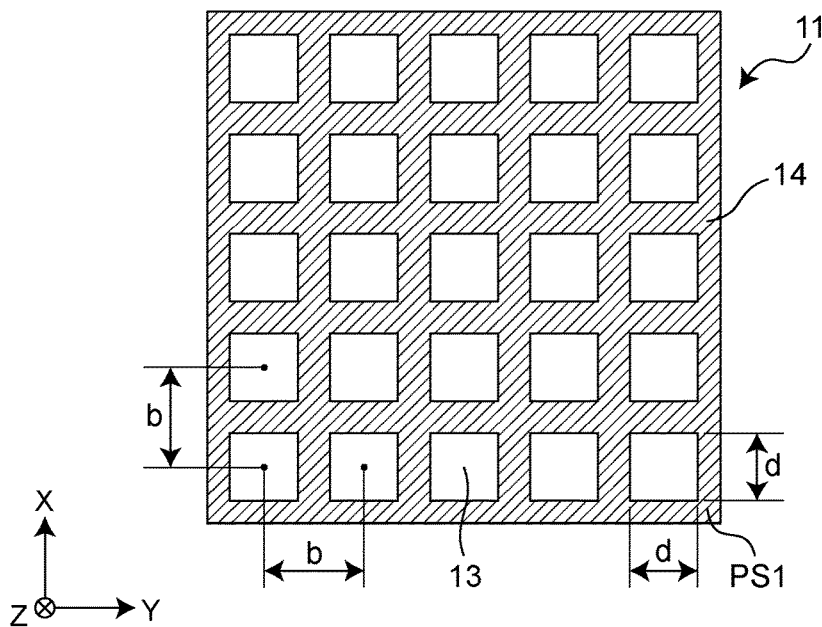
FIG. 6 is a schematic view of a part of the filter portion of FIG. 5 when viewed from a thickness direction.

FIG. 5 is an enlarged perspective view of a part of an example of the filter portion 11. FIG. 6 is a schematic view illustrating a part of the filter portion 11 of FIG. 5 when viewed from the thickness direction.

As illustrated in FIGS. 5 and 6, the filter portion 11 has a plate-like structure and has a first principal surface PS1 for capturing the filtration targets contained in the liquid and a second principal surface PS2 facing the first principal surface PS1. The filter portion 11 is formed with a plurality of through-holes 13 passing through the first principal surface PS1 and the second principal surface PS2. Specifically, the plurality of through-holes 13 are formed in a filter base portion 14 that constitutes the filter portion 11.

As illustrated in FIG. 2, a shape of the filter portion 11 is, for example, a circular shape, a rectangular shape, or an elliptical shape when viewed from the thickness direction (Z direction) of the filter 10. In accordance with an aspect of the disclosure, the shape of the filter portion 11 is substantially circular. Note that, in the specification, the term "substantially circular" means that the ratio of the length of the major axis to the length of the minor axis is 1.0 or more and 1.2 or less.

Referring back to FIGS. 5 and 6, the plurality of through-holes 13 are periodically arranged on the first principal surface PS1 and the second principal surface PS2 of the filter portion 11. Specifically, the plurality of through-holes 13 are arranged in a matrix at equal distances in the filter portion 11.

In an exemplary aspect, the through-hole 13 has a square shape when viewed from a side of the first principal surface PS1 of the filter portion 11, that is, the Z direction. Note that the shape of the through-hole 13 when viewed from the Z direction is not limited to a square shape, and may be, for example, a rectangular shape, a circular shape, or an elliptical shape.

In an exemplary aspect, a shape (sectional shape) of the through-hole 13 projected onto the surface perpendicular to the first principal surface PS1 of the filter portion 11 is a rectangular shape. Specifically, the sectional shape of the through-hole 13 is the rectangle shape in which the length of one side in the radial direction of the filter 10 is longer than the length of one side in the thickness direction of the filter 10.

In an exemplary aspect, when viewed from the side of the first principal surface PS1 (Z direction) of the filter portion 11, the plurality of through-holes 13 are arranged at equal distances in two arrangement directions parallel to the respective sides of the square, that is, in the X direction and the Y direction in FIG. 5. By arranging the plurality of through-holes 13 in a square lattice arrangement in this way, it is possible to increase the opening ratio and reduce the passing resistance of the liquid to the filter 10. With such a configuration, the filtration time can be shortened and the stress on the filtration targets can be reduced.

The arrangement of the plurality of through-holes 13 is not limited to the square lattice arrangement and may be, for example, a quasi-periodic arrangement or a periodic arrangement. As an example of the periodic arrangement, when it is a square arrangement, it may be a rectangular arrangement in which the distances in the two arrangement directions may not be equal to each other, or a triangular lattice arrangement, a regular triangular lattice arrangement, or the like. Note that the arrangement of the plurality of through-holes 13 is not limited as long as the plurality of through-holes 13 are provided in the filter portion 11.

The distance between the plurality of through-holes 13 is appropriately designed according to the type (size, shape, property, and elasticity) or amount of cells as filtration targets. Here, as illustrated in FIG. 6, the distance between the through-holes 13 means a distance b between a center of any through-hole 13 and a center of an adjacent through-hole 13 when the through-hole 13 is viewed from the side of the first principal surface PS1 of the filter portion 11. In a case of the structure of the periodic arrangement, when the shape of the through-hole 13 is square, the distance b between the through-holes 13 is, for example, larger than 1 time and 10 times or less of one side d of the through-hole 13, and preferably 3 times or less of one side d of the through-hole 13. Alternatively, for example, the opening ratio of the filter portion 11 is 10% or more, and preferably the opening ratio is 25% or more. With such a configuration, the passing resistance of the liquid to the filter portion 11 can be reduced. Therefore, the processing time can be shortened, and the stress on the cells can be reduced. The opening ratio is calculated by (area occupied by the through-holes 13)/ (projection area of the first principal surface PS1 assuming that the through-holes 13 are not provided).

A thickness of the filter portion 11 is preferably larger than 0.1 times and less than or equal to 100 times the size (i.e., one side d) of the through-hole 13. More preferably, the thickness of the filter portion 11 is larger than 0.5 times and less than or equal to 10 times the size (i.e., one side d) of the through-hole 13. With such a configuration, the resistance of the filter 10 to the liquid can be reduced, and the filtration time can be shortened. As a result, stress on the filtration targets can be reduced.

In the filter portion 11, it is possible that the first principal surface PS1 with which the liquid containing the filtration targets comes into contact have a small surface roughness. Here, the surface roughness means an average value of differences between the five maximum values and the five minimum values measured by the stylus step profiler at any curve on the first principal surface PS1. In accordance with an aspect of the disclosure, the surface roughness is preferably smaller than the size of the filtration targets, and is more preferably smaller than half of the size of the filtration targets. In other words, the openings of the plurality of through-holes 13 on the first principal surface PS1 of the filter portion 11 are formed on the same plane (XY plane). In addition, the filter base portion 14, which is a portion of the filter portion 11 in which the through-hole 13 may not be formed, is continuous and integrally formed. With such a configuration, the filtration targets are less likely to get stuck on the front surface (first principal surface PS1) of the filter portion 11, thus reducing the resistance of the liquid.

The through-hole 13 allows communication between an opening on the side of the first principal surface PS1 and an opening on a side of the second principal surface PS2 through a continuous wall surface. Specifically, the through-hole 13 is provided such that the opening on the side of the first principal surface PS1 can be projected onto the opening on the side of the second principal surface PS2. That is, when the filter portion 11 is viewed from the side of the first principal surface PS1, the through-hole 13 is provided such that the opening on the side of the first principal surface PS1 overlaps the opening on the side of the second principal surface PS2. In accordance with an aspect of the disclosure, the through-hole 13 is provided such that the inner wall thereof is perpendicular to the first principal surface PS1 and the second principal surface PS2.

A material used for the filter base portion 14 contains, as a main component, a metal and/or a metal oxide. The filter base portion 14 may be made of, for example, gold, silver, copper, platinum, nickel, palladium, titanium, an alloy thereof, or an oxide thereof. In particular, by using titanium or a nickel-palladium alloy, the elution of metal is reduced, and therefore the influence on the filtration targets can be reduced.

The frame portion 12 functions as a connection portion that connects the filter 10 and the holder 20.

Additionally, on the frame portion 12, information (for example, the size of the through-hole 13) of the filter may be indicated. This makes it easier to grasp the dimensions of the through-hole 13 without measuring the length again or the like and to distinguish between the front and back of the filter.

In accordance with an aspect of the disclosure, the filter 10 has a diameter of 17 mm and a thickness of 1.6 µm. The filter portion 11 has a diameter of 13 mm and the frame portion 12 has a width of 2 mm. The filter 10 is not limited to these dimensions and may be manufactured with other dimensions.

In accordance with an aspect of the disclosure, a material used for the frame portion 12 is the same as the material used for the filter portion 11 (the filter base portion 14). Note that the frame portion 12 and the filter portion 11 may not be integrally formed and may be formed of different materials.

As illustrated in FIG. 4A, the holder 20 has an inlet port 20a for pouring a liquid, a discharge port 20b for discharging the liquid, a flow path 20c through which the inlet port 20a and the discharge port 20b communicate, and a groove portion 21a formed on the outer periphery of the holder 20. The holder 20 holds the filter 10 in the flow path 20c between the inlet port 20a and the discharge port 20b. In accordance with an aspect of the disclosure, the holder 20 holds the filter 10 above the discharge port 20b in the flow path 20c.

The holder 20 is formed in a tubular shape. Specifically, in the holder 20, the inlet port 20a and the discharge port 20b are provided so as to face each other. Inside the holder 20, the flow path 20c is provided so as to allow communication between the inlet port 20a and the discharge port 20b.

In accordance with an aspect of the disclosure, the holder 20 has a first holder 21 having a tubular shape and a second holder 22 having a tubular shape and disposed inside the first holder 21.

As illustrated in FIGS. 2 and 4A, the first holder 21 has the groove portion 21a formed on the outer periphery thereof, and the grip section 23 is attached to the first holder 21 by inserting an insertion portion 23a of the grip section 23, which will be described later, into the groove portion 21a. As illustrated in FIG. 4B, in a state in which the insertion portion 23a of the grip section 23 is inserted into the groove portion 21a, a gap is formed between the insertion portion 23a and the groove portion 21a. Specifically, a width W2 of the groove portion 21a is larger than a thickness W1 of the grip section 23, and a distance D1 between an end surface 23aa of the insertion portion 23a and a bottom portion 21aa of the groove portion 21a is larger than 0. In other words, the gap is formed between the insertion portion 23a of the grip section 23 and the groove portion 21a in the width direction and the depth direction of the groove portion 21a. The width direction of the groove portion 21a is the Z direction in FIGS. 1 to 3, and the depth direction of the groove portion 21a is the XY direction in FIGS. 1 to 3. Note that the gap may be formed in at least one of the width direction and the depth direction of the groove portion 21a.

The width W2 of the groove portion 21a is set to be 1.1 times or more and less than 2 times the thickness W1 of the grip section 23. In order to prevent the grip section 23 from being unintentionally detached from the first holder 21, the width W2 of the groove portion 21a is preferably set to be 1.1 times or more and less than 1.5 times the thickness W1 of the grip section 23. Further, the distance D1 between the end surface 23aa of the insertion portion 23a of the grip section 23 and the bottom portion 21aa of the groove portion 21a is set to be 0.1 times or more and 0.8 times or less a depth D2 of the groove portion 21a. More preferably, the distance D1 is set to be 0.3 times or more and 0.6 times or less the depth D2.

By forming the gap between the insertion portion 23a and the groove portion 21a in this way, the first holder 21 can be moved within the range of the gap to the grip section 23. With this configuration, it is possible to apply vibration to the filter 10 held by the first holder 21 and the second holder 22 in a state in which the grip section 23 is fixed. Further, since there is the gap between the insertion portion 23a and the groove portion 21a, the grip section 23 can be easily detached from the holder 20.

In addition, inside the first holder 21, a pedestal portion 21b for holding the filter 10 is provided. The pedestal portion 21b protrudes from an inner wall of the first holder 21 toward the inside of the first holder 21, and is formed in a ring shape in the first holder 21. Note that the pedestal portion 21b may not be essential, and for example, a groove or the like for fitting the filter 10 may be formed in the first holder 21 or the second holder 22.

In accordance with an aspect of the disclosure, the first holder 21 has a shape in which two cylinders having different diameters are combined, but the shape of the first holder 21 is not limited thereto.

The second holder 22 is fitted into the first holder 21, and the filter 10 is held by the pedestal portion 21b of the first holder 21 and an end portion 22a of the second holder 22. In accordance with an aspect of the disclosure, a protruding portion 22b is formed on an outer periphery of the second holder 22, but the protruding portion 22b may not be essential.

The holder 20 including the first holder 21 and the second holder 22 may be formed of, for example, a resin material such as polyethylene, polystyrene, polypropylene, polycarbonate, polyetherimide, polyacetal, or polyether ether ketone. The first holder 21 and the second holder 22 may be formed in different colors. In this case, the first holder 21 and the second holder 22 may be easily distinguished by their colors. Accordingly, the orientation of the holder 20 may be easily determined.

The grip section 23 is formed in a flat plate shape, and has the insertion portion 23a to be inserted into the groove portion 21a of the first holder 21 and a grip section main body 23c. The grip section 23 is attached to the first holder 21 by inserting the insertion portion 23a into the groove portion 21a of the first holder 21. That is, the grip section 23 is formed as a component separate from the holder 20, and the grip section 23 is detachable from the holder 20.

The grip section 23 may be formed of, for example, a resin material such as polyethylene, polystyrene, polypropylene, polycarbonate, polyetherimide, polyacetal, or polyether ether ketone. The grip section 23 may be formed of the same material as the first holder 21 and the second holder 22 or may be formed of a different material. In addition, the grip section 23 may be formed in a different color from the first holder 21 and/or the second holder 22.

The grip section main body 23c is provided with a through-hole 23d into which the holder 20 is inserted. The insertion portion 23a is an inner wall of the through-hole 23d. Alternatively, part of an upper surface and a lower surface of the grip section main body 23c connected to the inner wall of the through-hole 23*d* may also be included in the insertion portion 23*a*. Four notch portions 23*b* are formed in the insertion portion 23*a* and the insertion portion 23*a* is divided into a plurality of portions by the notch portions 23*b*. Further, the notch portion 23*b* may be connected to an outer periphery of the grip section main body 23*c*. By being connected to the outer periphery of the grip section body 23*c*, the insertion portion 23*a* can be inserted into the groove portion 21*a* of the first holder 21 by moving the grip section 23 in the plane direction on the flat plate.

The through-hole 23*d* is provided so that an inner diameter R1 thereof is larger than a diameter of the bottom portion 21*aa* (see FIG. 4B) of the groove portion 21*a* and is smaller than a diameter of the outer periphery of the first holder 21 when the first holder 21 is viewed from the Z-direction, so as to satisfy the relationship between the groove portion 21*a* of the first holder 21 and the insertion portion 23*a* of the grip section 23 described above. In accordance with an aspect of the disclosure, the first holder 21 has the shape in which two cylinders having different diameters are combined, and the outer periphery in this case corresponds to the outer periphery on which the groove portion 21*a* is formed. By providing the through-hole 23*d* in this way, when the grip section 23 is connected to the first holder 21, a gap can be formed between the insertion portion 23*a* and the groove portion 21*a*.

The four notch portions 23*b* are formed in the insertion portion 23*a*. Accordingly, the insertion portion 23*a* is divided into four. Further, the notch portions 23*b* are provided at equal distances around the holder 20. The expression "provided at equal distances around the holder 20" means that, as illustrated in FIG. 3, the respective notch portions 23*b* are arranged so as to be rotationally symmetric with respect to the center of the holder 20. In accordance with an aspect of the disclosure, the respective notch portions 23*b* are arranged at distances of 90 degrees around the holder 20. Note that the arrangement distances of the notch portions 23*b* are not limited to the above as long as the distances are equal. In this case, the respective insertion portions 23*a* are arranged so as to be rotationally symmetric with the first holder 21 as a central axis. According to such a configuration, it is possible to improve stability when the grip section 23 is attached to the first holder 21. Note that the notch portion 23*b* may not be essential and may not be provided. Further, the notch portions 23*b* may not be provided at equal distances.

As illustrated in FIG. 2, the first holder 21 and the grip section 23 can be connected by inserting the first holder 21 into the through-hole 23*d* of the grip section 23 from the Z direction. Due to the size relationship between the insertion portion 23*a* and the groove portion 21*a* described above, the inner diameter R1 of the through-hole 23*d* is smaller than the outer diameter of the first holder 21. However, by pushing the first holder 21 into the through-hole 23*d* in the Z direction, the insertion portion 23*a* bends due to the stress. Thereby the insertion portion 23*a* can be inserted into the groove portion 21*a*, so that the first holder 21 and the grip section 23 can be connected to each other. With such a configuration, in a state in which the grip section 23 is connected to the first holder 21, the gap is formed between the groove portion 21*a* and the insertion portion 23*a*. For this reason, when the grip section 23 is fixed, the holder 20 can be vibrated. On the contrary, when the holder 20 is fixed, the grip section 23 can be rotated.

Figure 7:
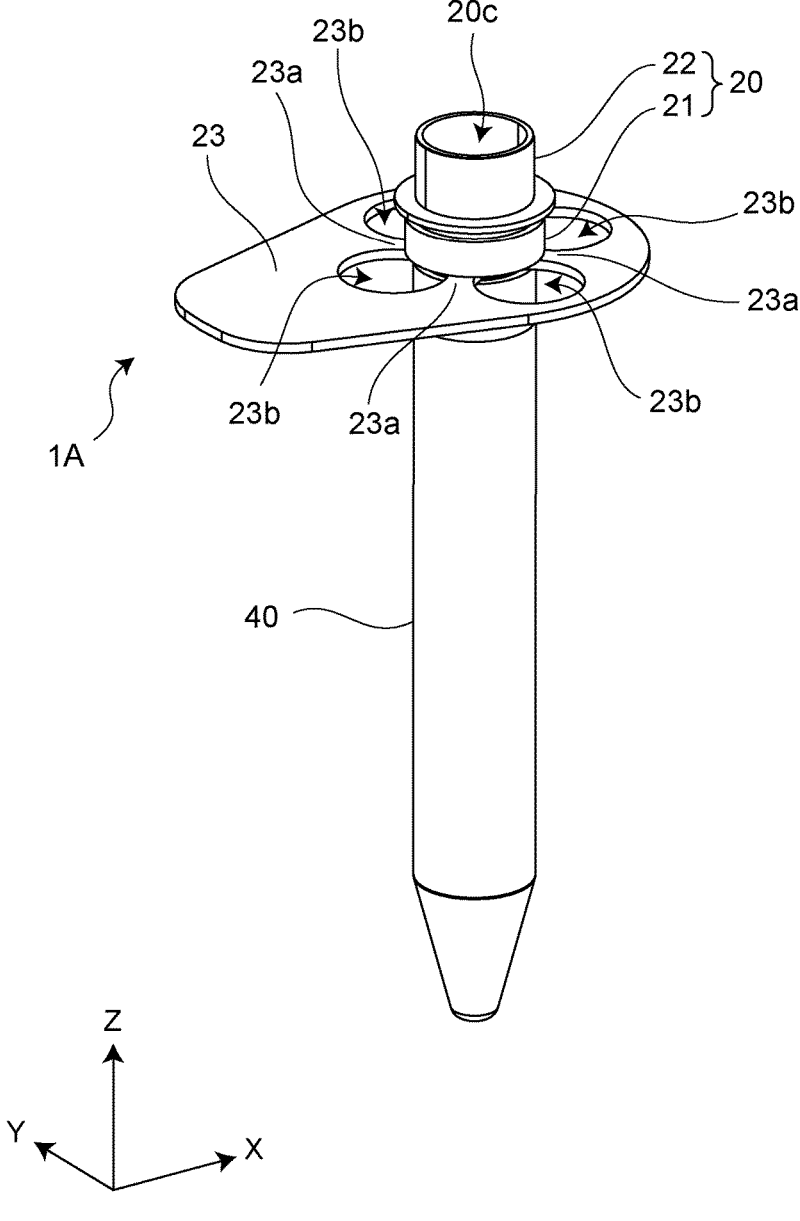
FIG. 7 is a schematic view illustrating a state in which the filtration and collection device in accordance with aspects of the present disclosure as attached to a centrifuge tube.

FIG. 7 is a schematic view illustrating a state in which the filtration and collection device 1A according to an aspect of the present disclosure, and is attached to a centrifuge tube 40. As illustrated in FIG. 7, by having the grip section 23, the filtration and collection device 1A is held in the centrifuge tube 40 by the grip section 23. Specifically, when the filtration and collection device 1A is attached to an opening of the centrifuge tube 40, the grip section 23 is placed on an opening end portion that defines the opening of the centrifuge tube 40. In this way, the grip section 23 is held by the opening end portion of the centrifuge tube 40.

When the filtration and collection device 1A is attached to the centrifuge tube 40, the four notch portions 23*b* formed in the insertion portion 23*a* of the grip section 23 serve as vent holes for passing air between the inside and the outside of the centrifuge tube 40. Thus, it may be possible to prevent the internal pressure of the centrifuge tube 40 from rising. That is, since the pressure difference between the inside and the outside of the centrifuge tube 40 becomes small, it is possible to reduce the passing resistance of the liquid due to the increase in the internal pressure of the centrifuge tube 40 when the liquid is poured into the filtration and collection device 1A. With such a configuration, the filtration time can be shortened and the stress on the filtration targets may be reduced.

Further, since the notch portion 23*b* is formed in the insertion portion 23*a* of the grip section 23, in a state in which the filtration and collection device 1A is attached to the centrifuge tube 40, the state of the liquid discharged to the centrifuge tube 40 can be visually checked through the notch portion 23*b*.

Further, for example, an additional liquid such as a reagent may be poured into the liquid discharged to the centrifuge tube 40 or a part of the liquid discharged to the centrifuge tube 40 may be extracted, with a pipette or the like through the notch portion 23*b*.

One or a plurality of convex portions may be provided at a portion where the grip section 23 contacts the centrifuge tube 40. According to such a configuration, while the liquid is being poured into the filtration and collection device 1A, the holder 20 is more likely to be vibrated, and the liquid permeability and the collection rate of the filtration targets can be improved.

An example of a method for filtering and collecting a suspension by the filtration and collection device 1A will be described.

As illustrated in FIG. 7, the filtration and collection device 1A is attached to the centrifuge tube 40. At this time, the grip section 23 is held by the opening end portion of the centrifuge tube 40.

A liquid containing the filtration targets is poured into the flow path 20*c* inside the holder 20 from the inlet port 20*a* of the holder 20 of the filtration and collection device 1A. Since the gap is formed between the insertion portion 23*a* of the grip section 23 and the groove portion 21*a* of the first holder 21, the holder 20 can be vibrated when the grip section 23 is fixed to the opening end portion of the centrifuge tube 40. Therefore, while the liquid is being poured, the holder 20 vibrates irregularly due to the impact when the liquid flows. Due to this irregular vibration, filtration targets that are smaller than the through-holes 13 and attached to the filter base portion 14 of the filter 10 fall into the centrifuge tube 40, so that clogging of the filter 10 can be prevented. As a result, it is also possible to improve liquid permeability.

The liquid discharged into the centrifuge tube 40 is extracted with a pipette or the like. The liquid discharged into the centrifuge tube 40 includes filtration targets smaller than a desired size, that is, filtration targets having a size sufficient to pass through the through-holes 13 of the filter portion 11.

The filter 10 is detached from the holder 20, and is put into, for example, a buffer solution to isolate the filtration targets attached to the filter 10.

In this way, it is possible to separate the filtration targets having sizes sufficient to pass through the through-holes 13 of the filter 10 and the filtration targets having sizes larger than the through-holes 13.

According to the filtration and collection device 1A according to an aspect of the present disclosure, the following effects can be obtained.

The filtration and collection device 1A includes the holder 20, the filter 10, and the grip section 23. The holder 20 has the inlet port 20a, the discharge port 20b, the flow path 20c through which the inlet port 20a and the discharge port 20b communicate, and the groove portion 21a formed on the outer periphery of the holder 20. The filter 10 is disposed in the flow path 20c of the holder 20 and has the plurality of through-holes 13. The grip section 23 has the insertion portion 23a that is inserted into the groove portion 21a. The gap is formed between the groove portion 21a and the insertion portion 23a. Therefore, when the liquid is poured into the filtration and collection device 1A in a state in which the grip section 23 is fixed, the holder 20 can be vibrated.

With such a configuration, when the liquid containing the filtration targets is poured into the filtration and collection device 1A, the filtration targets smaller than the through-holes 13 and attached to the filter base portion 14 of the filter 10 fall into the centrifuge tube 40. Thus, the occurrence of clogging can be reduced and the liquid permeability can be improved.

Further, due to the gap between the groove portion 21a and the insertion portion 23a, the grip section 23 can be rotated around the holder 20 when the holder 20 may be fixed. For example, when observing with a microscope while the filter 10 is attached to the holder 20, even when the grip section 23 is accidentally touched, the grip section 23 rotates, so that the observation range is prevented from being shifted.

In addition, the filtration and collection device 1A can be disassembled into the filter 10, the holder 20, and the grip section 23. For example, when a plurality of filtration and collection devices 1A are packed in the same container to be transported or stored, the grip section 23 connected to a certain filtration and collection device 1A may come into contact with the filter 10 of another filtration and collection device 1A, thereby damaging the filter 10. However, according to the present invention, by disassembling the holder 20 and the grip section 23, it is possible to prevent the filter 10 from being damaged by the grip section 23 during packaging.

Since the grip section 23 is detachable from the holder 20, the plurality of filtration and collection devices 1A can be stacked to use without interfering the grip sections 23 with each other.

Further, since the grip section 23 is detachable from the holder 20, it is possible to use a large number of filtration and collection devices 1A side by side on a flat plane without interfering the grip sections 23 with each other. A plurality of liquid storage containers, such as the centrifuge tubes 40, each of which is connected to a cell strainer in which the grip section 23 is fixed to the holder 20, may be simultaneously used on the same plane. In this case, in order to prevent the plurality of grip sections 23 from interfering with each other, a certain arrangement distance is required between the liquid storage containers. For this reason, it may be difficult to simultaneously use a plurality of cell strainers in a limited work plane. For example, as illustrated in FIG. 3, when viewed from the Z direction, outside a circle C1 in which the filtration and collection device 1A fits, the liquid storage container to which the adjacent filtration and collection device 1A is connected is disposed.

However, when the grip section 23 is detached from the holder 20, it is possible to bring the liquid storage container, to which the adjacent filtration and collection device 1A is connected, close to a circle C2 illustrated in FIG. 3, that is, the outer periphery of the holder 20. Thus, in a limited work plane, a large number of filtration and collection devices 1A can be simultaneously used.

Further, the plurality of notch portions 23b are formed in the insertion portion 23a. In this case, when the filtration and collection device 1A is attached to, for example, the centrifuge tube 40, the plurality of notch portions 23b serve as vent holes for passing air between the inside and the outside of the centrifuge tube 40, thereby preventing the internal pressure of the centrifuge tube 40 from rising. Therefore, it is possible to further improve the liquid permeability.

Further, the plurality of notch portions 23b are formed at equal distances to the holder 20. In this case, it is possible to improve stability when the grip section 23 is attached to the holder 20.

Further, the grip section 23 may be formed in the flat plate shape and have the principal surface, and one or a plurality of convex portions may be formed on the principal surface. In this case, while the liquid is poured into the filtration and collection device 1A, the holder 20 is more likely to be vibrated, and the liquid permeability and collection rate of the filtration targets can be improved.

The filter 10 contains, as a main component, at least one of a metal and a metal oxide. With such a configuration, the filtration targets can be easily collected, and the collection rate can be improved. For example, since the resin filter has variations in the size and the arrangement of the through-holes, the filtration targets may be trapped in the through-holes. The filter 10 containing, as a main component, at least one of a metal and a metal oxide is designed so that the size and the arrangement of the through-holes are more uniform than those of the resin filter. Therefore, in the filtration and collection device 1A, by using the filter 10 containing, as a main component, at least one of a metal and a metal oxide, when the filtration targets are collected, the filtration targets can be easily peeled off from the filter 10 and the collection rate can be improved as compared to the resin filter.

Note that, in an exemplary aspect, the filter 10 is a metal filter is described, but the present disclosure is not limited to this example. The filter 10 may be a film-like or sheet-like material capable of separating, by filtration, the filtration targets contained in a liquid.

In an exemplary aspect, the filtration and collection device 1A is provided with one filter 10 is described, but the present disclosure is not limited to this example. The filtration and collection device 1A may include a plurality of filters. When the filtration and collection device 1A includes a plurality of filters, the plurality of filters may be arranged in series in a direction in which the liquid flows. Further, the dimensions of the through-holes of the plurality of filters may be different from each other. For example, the plurality of filters may be arranged in series in descending order of the size of the through-holes from the upstream side through which the liquid flows. With such a configuration, it is possible to separate, by filtration, and collect filtration targets of different sizes at one time.

In an exemplary aspect the filtration targets are described as cells, and the liquid is described as a cell suspension, but the present disclosure is not limited thereto.

In exemplary aspect the holder 20 is constituted of the first holder 21 and the second holder 22 is described, but the present disclosure is not limited to this example. The holder 20 may have the first holder 21 and the second holder 22 which are integrally formed or may be constituted of two or more parts.

In an exemplary aspect the frame portion 12 of the filter 10 is held by the first holder 21 and the second holder 22 over the entire circumference, but the present invention is not limited to this example. For example, the frame portion 12 may be partially held by the first holder 21 and the second holder 22. With such a configuration, it is possible to suppress the tensile stress applied to the filter 10 in the radial direction. As a result, it is possible to suppress damage to the filter 10 during the filtration.

In an exemplary aspect the filtration and collection device 1A are attached to the centrifuge tube 40 during the filtration, but the present disclosure is not limited to this example. When filtration, the filtration and collection device 1A may be attached to a container other than the centrifuge tube, a device, or the like.

In an exemplary aspect the filter 10 is disposed substantially perpendicular to the inner wall of the holder 20 is described, but the present disclosure is not limited to this example. The filter 10 may be disposed obliquely with respect to the inner wall of the holder 20.

In addition, in an exemplary aspect the four notch portions 23b are formed is described, but the present disclosure is not limited to this example. One or a plurality of notch portions 23b may be provided.

Figure 8A:
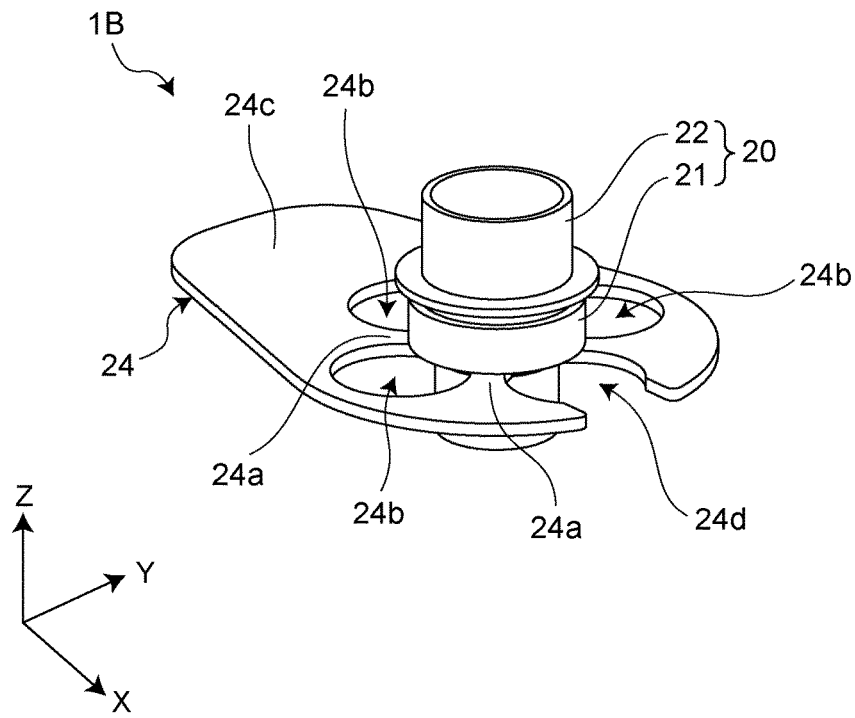
FIG. 8A is a schematic perspective view of a filtration and collection device of a modified example in accordance with aspects of the present disclosure.
Figure 8B:
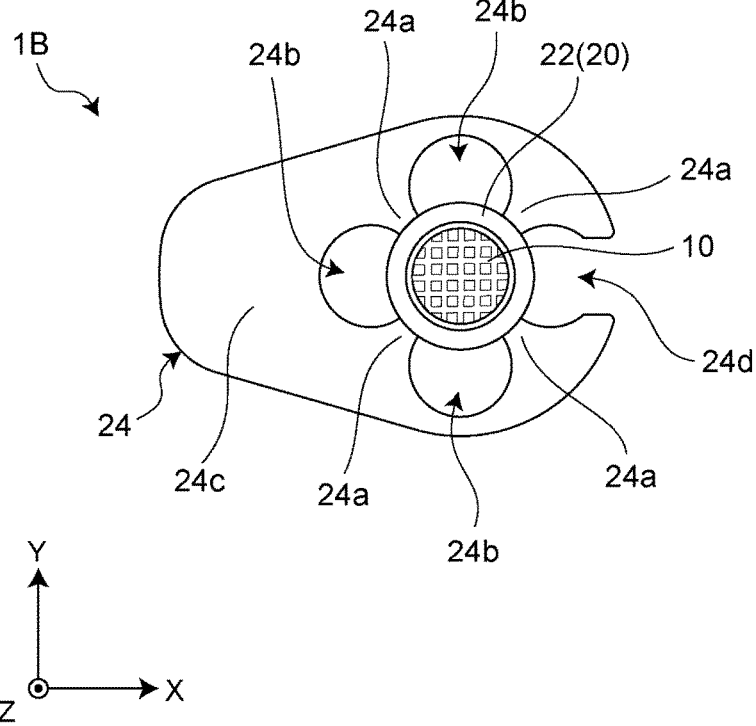
FIG. 8B is a schematic plan view of the filtration and collection device of FIG. 8A.
Figure 8C:
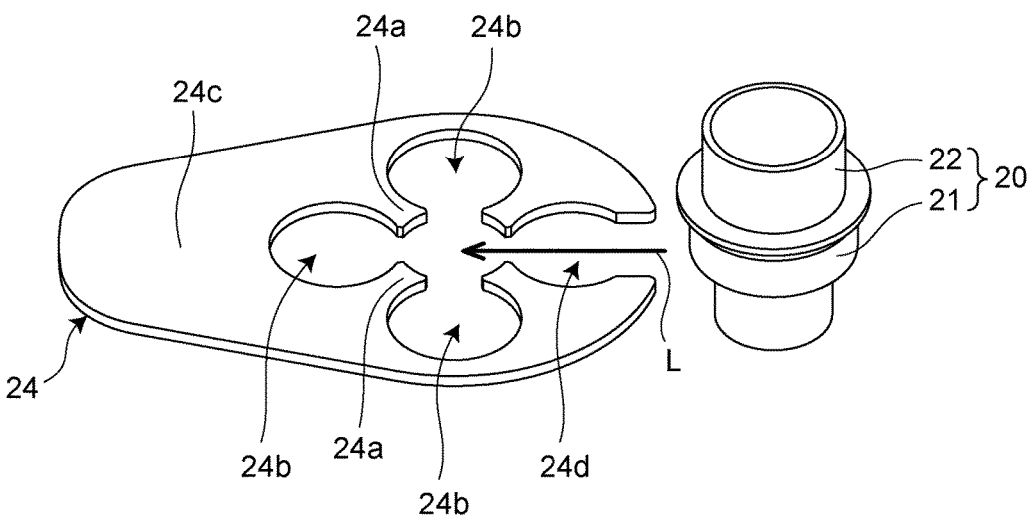
FIG. 8C is an exploded perspective view of the filtration and collection device of FIG. 8A.

FIG. 8A is a schematic perspective view of a filtration and collection device 1B according to a modified example of an aspect of the disclosure. FIG. 8B is a schematic plan view of the filtration and collection device 1B of FIG. 8A. FIG. 8C is an exploded perspective view of the filtration and collection device 1B of FIG. 8A.

As in the filtration and collection device 1B illustrated in FIGS. 8A to 8C, a grip section 24 may be formed in a recessed shape when viewed from the Z direction. The phrase "the grip section 24 is formed in a recessed shape" means that a notch portion 24d, which is one of notch portions, is formed in connection with an outer periphery of a grip section main body 24c. Note that the notch portion 24d formed in connection with the outer periphery is not limited to that illustrated in FIGS. 8A to 8C, and any notch portion 24d may be formed in connection with the outer periphery. As illustrated in FIG. 8C, by moving the holder 20 to the notch portion 24b connected to the outer periphery of the grip section main body 24c in a direction indicated by arrow L, the holder 20 can be connected to the grip section 24. For this reason, the grip section 24 and the holder 20 can be more easily attached and detached.

Figure 9:
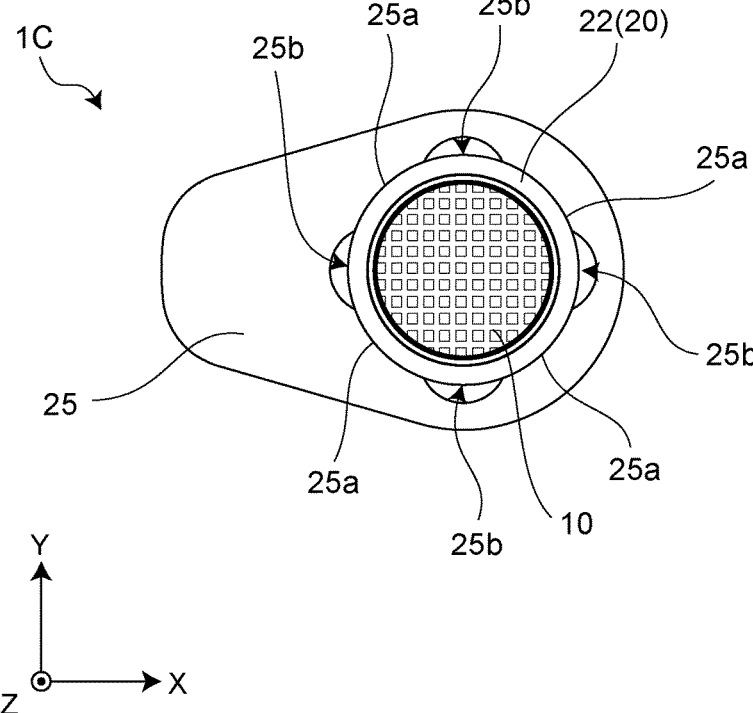
FIG. 9 is a schematic plan view of a filtration and collection device of another modified example in accordance with aspects of the present disclosure.

FIG. 9 is a schematic plan view of a filtration and collection device 1C of another modified example according an aspect of the disclosure. As illustrated in FIG. 9, the shape and size of a notch portion 25b provided in an insertion portion 25a of a grip section 25 may be different from that of the notch portion 23b.

By making the size of the notch portion 25b smaller than the size of the notch portion 23b described above, the portion acting as a vent hole between the inside and the outside of the centrifuge tube 40 becomes small. Thus, it is possible to slow down the speed at which the liquid passes through the filter 10. By adjusting the size of the notch portion in this way, it is possible to adjust the speed at which the liquid passes through the filter 10.

Further, in this case, since the insertion portion 25a is formed to be wider than the above-described insertion portion 23a, it is possible to improve stability when the grip section 25 is connected to the holder 20.

A filtration and collection device according to an aspect of the disclosure will be described.

In accordance with an aspect of the disclosure, points different as described above will be mainly described. In accordance with an aspect of the disclosure, the same or equivalent configurations as those described above will be denoted with the same reference numerals. In addition, in accordance with an aspect of the disclosure, description overlapping with the disclosure described above will be omitted.

In accordance with an aspect of the disclosure a filtration and collection device has a plurality of grip sections.

Figure 10:
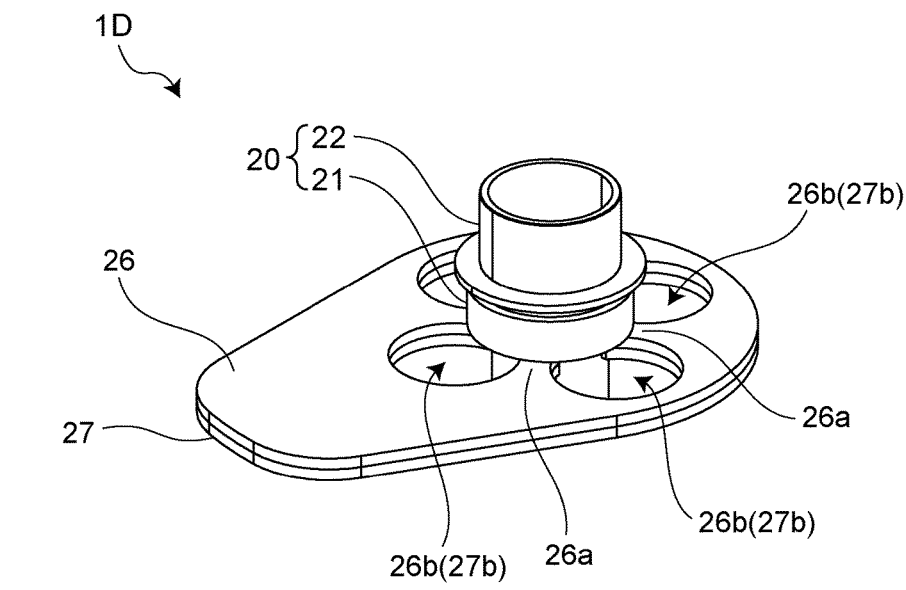
FIG. 10 is a schematic configuration diagram of an example of a filtration and collection device in accordance with aspects of the present disclosure.
Figure 10:
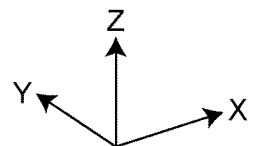
Figure 11:
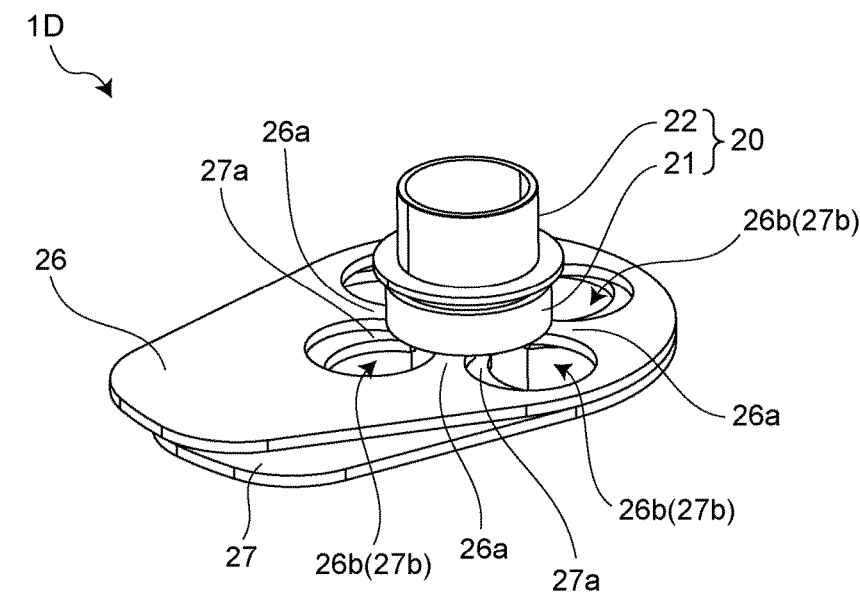
FIG. 11 is another schematic configuration diagram of the filtration and collection device of FIG. 10.
Figure 11:
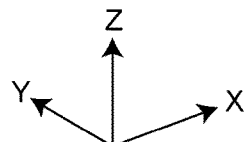
Figure 12:
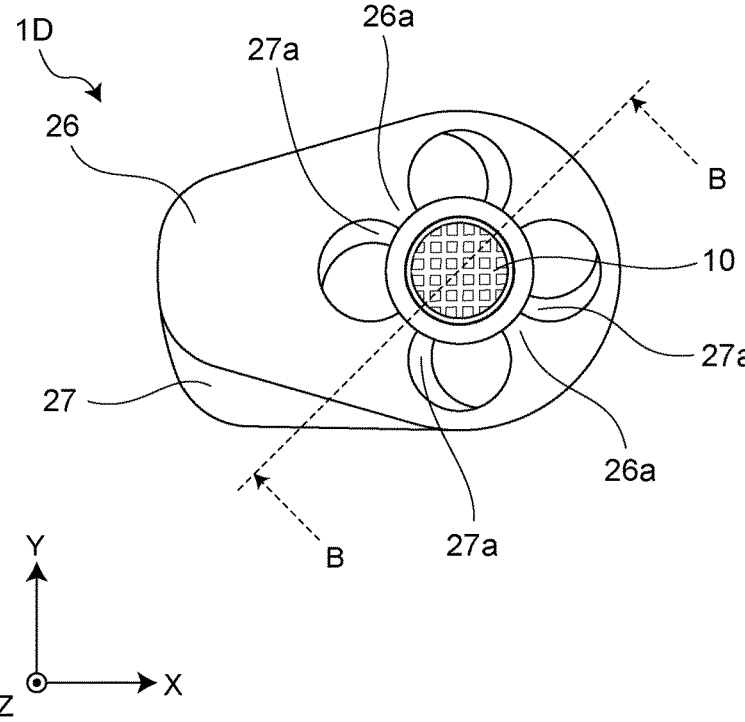
FIG. 12 is a plan view of the filtration and collection device of FIG. 10.
Figure 13A:
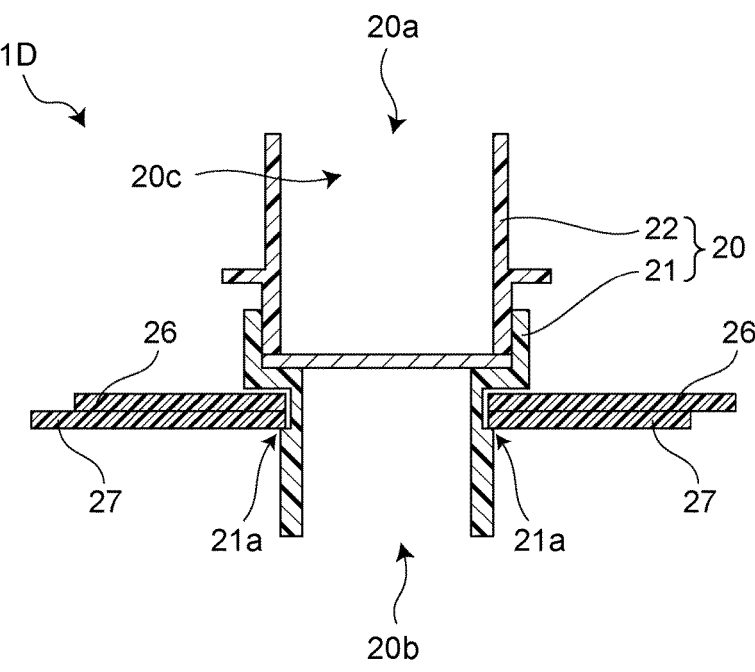
FIG. 13A is a sectional view taken along line B-B of the filtration and collection device of FIG. 11.
Figure 13B:
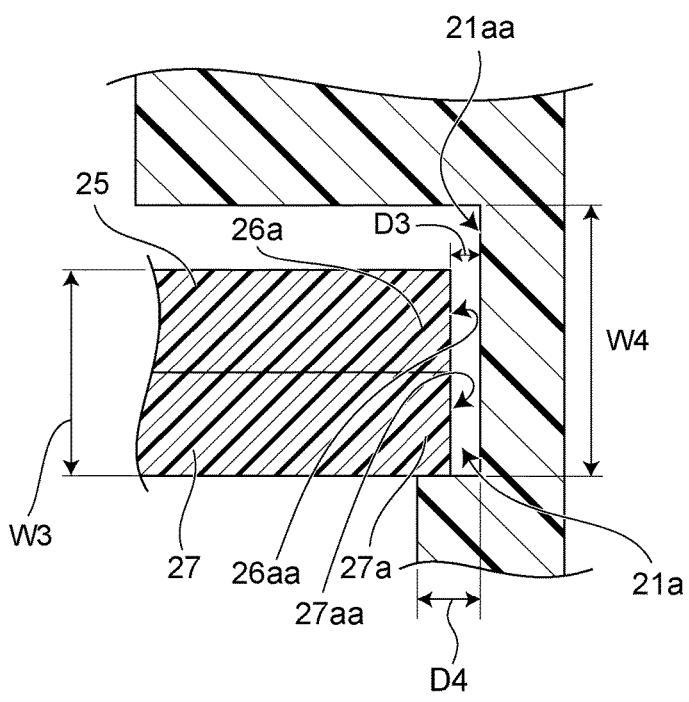
FIG. 13B is an enlarged sectional view of a part of the filtration and collection device of FIG. 13A.

FIG. 10 is a schematic configuration diagram of an example of a filtration and collection device 1D according an aspect of the disclosure. FIG. 11 is another schematic configuration diagram of the filtration and collection device 1D of FIG. 10. FIG. 12 is a plan view of the filtration and collection device 1D of FIG. 10. FIG. 13A is a sectional view taken along line B-B of the filtration and collection device 1D of FIG. 12. FIG. 13B is an enlarged sectional view illustrating a part of the filtration and collection device 1D of FIG. 13A.

As illustrated in FIGS. 10 to 12, the filtration and collection device 1D includes a plurality of grip sections 26 and 27. The plurality of grip sections 26 and 27 are formed in a flat plate shape, and are arranged so as to be stacked in the thickness direction (Z direction). As illustrated in FIG. 10, in accordance with an aspect of the disclosure, the plurality of grip sections 26 and 27 having the same shape are arranged so as to be stacked in the thickness direction. The grip section 26 has an insertion portion 26a and a notch portion 26b. Similarly, the grip section 27 has an insertion portion 27a and a notch portion 27b. As illustrated in FIGS. 11 and 12, the grip section 26 and the grip section 27 can be individually rotated about the holder 20. With such a configuration, the size of the hole formed by the two notch portions 26b and 27b can be changed. When the filtration and collection device 1D is attached to, for example, a centrifuge tube, the hole formed by the two notch portions 26b and 27b functions as a vent hole between the inside and the outside of the centrifuge tube.

As illustrated in FIG. 13A, in accordance with an aspect of the disclosure, by inserting the insertion portion 26a of the grip section 26 and the insertion portion 27a of the grip section 27 into the groove portion 21a formed in the first holder 21, the grip section 26 and the grip section 27 are attached to the first holder 21. As illustrated in FIG. 13B, in the groove portion 21a, a gap is formed between the insertion portion 26a and the insertion portion 27a and the groove portion 21a when the grip section 26 and the grip section 27 are inserted into the groove portion 21a. Specifically, a width W4 of the groove portion 21a is larger than a thickness W3 formed when the grip section 26 and the grip section 27 are stacked, and a distance D3 between an end surface 26aa of the insertion portion 26a or an end surface 27aa of the insertion portion 27a and the bottom portion 21aa of the groove portion 21a is larger than 0. That is, the gap is formed between the insertion portion 26a of the grip section 26 and the insertion portion 27a of the grip section 27 and the groove portion 21a in the width direction and the depth direction of the groove portion 21a. The width direction of the groove portion 21a is the Z direction in FIGS. 10 to 12, and the depth direction of the groove portion 21a is the XY direction in FIGS. 10 to 12. Note that the gap may be formed in at least one of the width direction and the depth direction of the groove portion 21*a*.

The width W4 of the groove portion 21*a* is set to be 1.1 times or more and less than 2 times the thickness W3 when the grip section 26 and the grip section 27 are stacked. In order to prevent the grip section 26 and the grip section 27 from being unintentionally detached, the width W4 of the groove portion 21*a* is preferably set to be 1.1 times or more and less than 1.5 times the thickness W3 when the grip section 26 and the grip section 27 are stacked. Further, the distance D3 between the end surface 26*aa* of the insertion portion 26*a* and the end surface 27*aa* of the insertion portion 27*a* and the bottom portion 21*aa* of the groove portion 21*a* is set to 0.1 times or more and 0.8 times or less the depth D4 of the groove portion 21*a*. More preferably, the distance D3 is set to be 0.3 times or more and 0.6 times or less of the depth D4.

Note that the grip section 26 and the grip section 27 may be formed so as to have different thicknesses.

According to the filtration and collection device 1D according to accordance with an aspect of the disclosure, the following effects can be obtained.

In the filtration and collection device 1D, the two grip sections 26 and 27 are arranged so as to be stacked in the thickness direction. With such a configuration, when the filtration and collection device 1D is attached to, for example, a centrifuge tube, by rotating either the grip section 26 or the grip section 27, the size of the vent hole for passing air between the inside and the outside of the centrifuge tube can be changed. Note that the vent hole is a hole formed by the two notch portions 26*b* and 27*b* described above. For example, by changing the size of the vent hole while pouring the liquid into the filtration and collection device 1D, the speed at which the liquid passes through the filter 10 can be adjusted.

In an exemplary aspect, "Example 1," cell aggregations and single cells contained in a cell suspension were separated using the filtration and collection device 1A as described above. Then, the cell suspension that passed through the filter 10 and the cell aggregations that were captured by the filter 10 were evaluated. The evaluation was also performed using Comparative Example 1 under the same conditions as described above.

Since the configuration of the filtration and collection device 1A of Example 1 is described above, the description thereof will be omitted.

Figure 14:
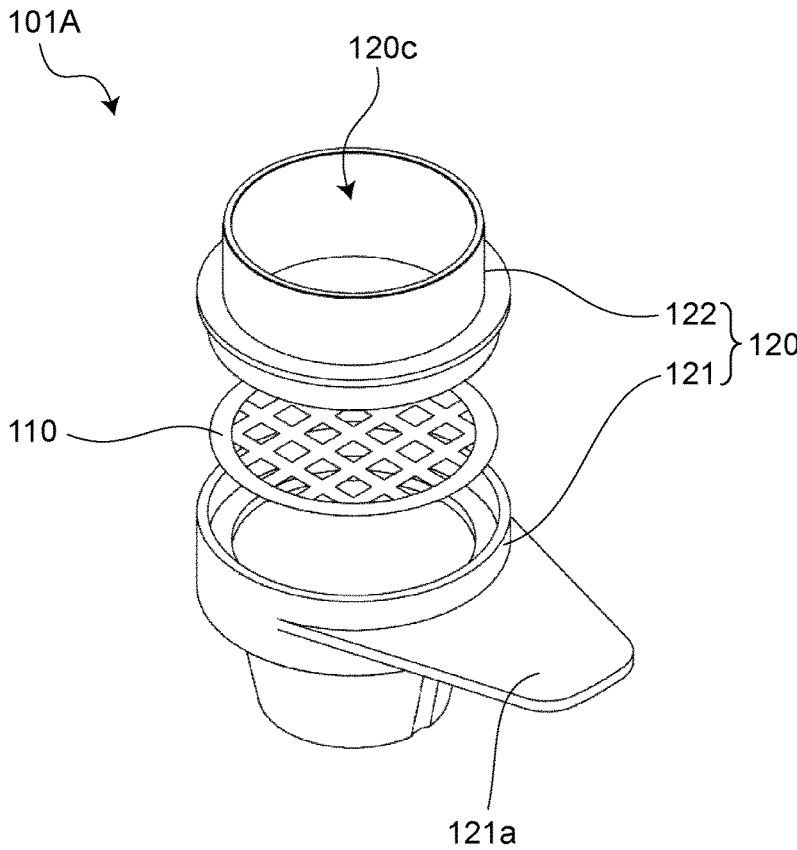
FIG. 14 is a schematic configuration diagram of a filtration and collection device in accordance with aspects of the present disclosure.

FIG. 14 is a schematic configuration diagram of a filtration and collection device 101A of Comparative Example 1. As illustrated in FIG. 14, the filtration and collection device 101A of Comparative Example 1 includes a holder 120 having an inlet port, a discharge port, and a flow path 120*c* through which the inlet port and the discharge port communicate, and a filter 110 arranged in the flow path 120*c*. The holder 120 has a first holder 121 in which a grip section 121*a* is integrally formed and a second holder 122 which is fitted into the first holder 121. Other configurations are the same as those of the filtration and collection device 1A of Example 1.

The filtration and collection device 1A of Example 1 and the filtration and collection device 101A of Comparative Example 1 were provided with the same filter. The filter has square through-holes in a square lattice arrangement, and the length d of one side of the square (see FIG. 6) is 30 μm, the lattice distance b (see FIG. 6) is 42 μm, and the thickness of the filter is 1.6 μm. In addition, the material of the filter is Ni.

Figure 15:
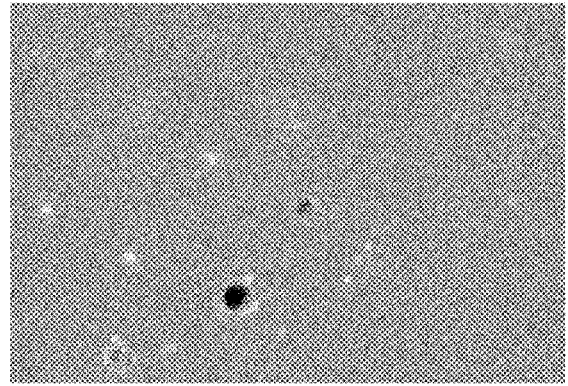
FIG. 15 is a photomicrograph of a prepared cell suspension.

2 ml of DMEM medium (1 g/L Glucose with L-Glutamine and Sodium Pyruvate—10% FBS) was added to each well of micro-space cell culture plate (product number MPc 500 6) manufactured by Kuraray Co., Ltd., and $1\times10^6$ mouse embryonic fibroblasts (MEFs) were seeded per well to prepare cell aggregations. On 7th day from the start of culturing, cell aggregations were extracted from the plate and adjusted with DMEM medium to prepare 20 ml of a cell suspension having a cell aggregation concentration of 30 cells/ml. The cell suspension was observed under a microscope. The average value, the minimum value, and the maximum value of the spherically approximated diameters of ten cell aggregations were measured, and as a result, 110±40 μm was obtained. FIG. 15 is a photomicrograph of the prepared cell suspension. As illustrated in FIG. 15, three cell aggregations and 16 single cells that may not completely become cell aggregations were observed. Note that the field of view area of the microscope is 1.70×1.17 mm². In the photomicrograph of FIG. 15, the large aggregations are the cell aggregations and white spherical images are single cells. Note that the microscope is out of focus on the single cells, and thus the sizes of the single cells seem to be larger than they actually are.

The filtration and collection device 1A of Example 1 and the filtration and collection device 101A of Comparative Example 1 were attached to the respective centrifuge tubes of 50 ml. Then, the cell suspension mentioned above was poured into the respective filtration and collection devices by 10 ml each, and then, 40 ml each of phosphate buffered saline (PBS) was poured.

While the cell suspension and PBS were poured into the filtration and collection device 1A of Example 1, it was visually observed that the filtration and collection device 1A vibrated irregularly on the centrifuge tube with a rattling noise.

On the other hand, while the cell suspension and PBS were poured into the filtration and collection device 101A of Comparative Example 1, it was visually observed that the filtration and collection device 101A remained on the centrifuge tube without vibration.

Twenty seconds after pouring the cell suspension and PBS, the amount of liquid in the centrifuge tube was visually measured using a centrifuge tube scale. The amount of liquid in the centrifuge tube was 48 ml in Example 1 and 44 ml in Comparative example 1.

Figure 16:
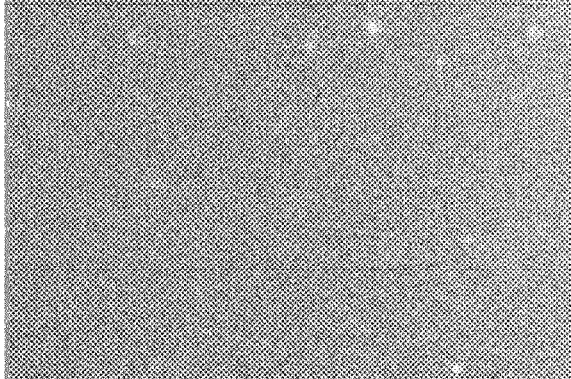
FIG. 16 is a photomicrograph of a liquid discharged from the filtration and collection device in accordance with aspects of the present disclosure.
Figure 17:
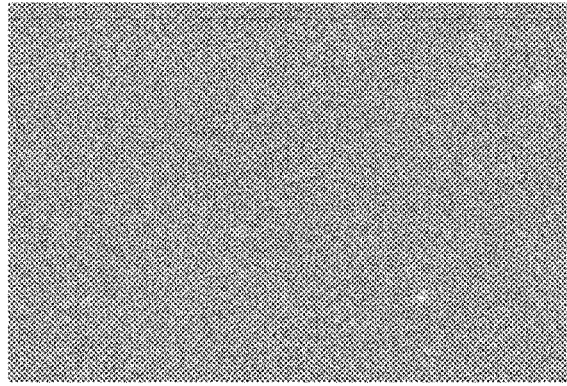
FIG. 17 is a photomicrograph of a liquid discharged from the filtration and collection device in accordance with aspects of the present disclosure.

The liquid discharged into the centrifuge tube was extracted with a pipette and observed with a microscope. FIG. 16 is a photomicrograph of the liquid discharged from the filtration and collection device 1A of Example 1. FIG. 17 is a photomicrograph of the liquid discharged from the filtration and collection device 101A of Comparative Example 1. Note that the field of view area of the microscope is 1.70×1.17 mm².

As shown in FIG. 16, 14 single cells were observed in Example 1. On the other hand, as shown in FIG. 17, five single cells were observed in Comparative Example 1.

Next, the cells captured by the filter were observed. Filters detached from the filtration and collection devices of Example 1 and Comparative Example 1 were put into respective 20 ml beakers with 10 ml of PBS added, and cells attached to the filter were isolated. The liquid in the beaker was observed under a microscope.

Figure 18:
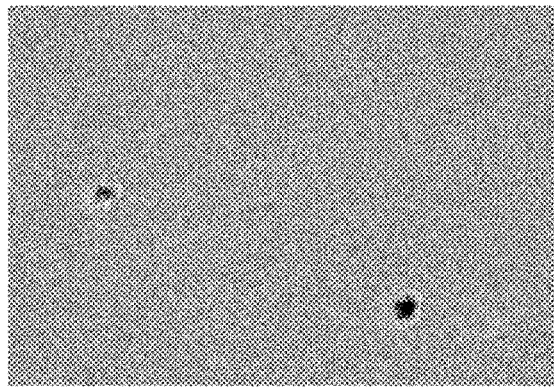
FIG. 18 is a photomicrograph of cells captured by the filtration and collection device in accordance with aspects of the present disclosure.
Figures 19, 20:
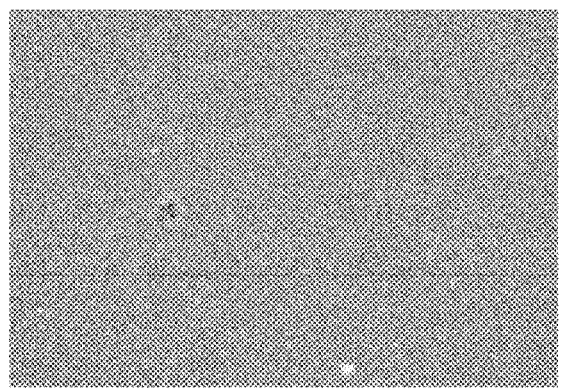
FIG. 19 is a photomicrograph of cells captured by the filtration and collection device in accordance with aspects of the present disclosure.
FIG. 20 is a table showing results of microscopic observations in accordance with aspects of the present disclosure.

FIG. 18 is a photomicrograph of cells captured by the filtration and collection device 1A of Example 1. FIG. 19 is a photomicrograph of cells captured by the filtration and collection device 101A of Comparative Example 1. Note that the field of view area of the microscope is 1.70×1.17 mm².

In both Example 1 and Comparative Example 1, cell aggregation(s) were observed. As shown in FIG. 18, in Example 1, two cell aggregations were observed, and one single cell was further observed. In FIG. 18, a particulate matter seen between the center and upper right is a fine particle other than a cell.

As shown in FIG. 19, in Comparative Example 1, one cell aggregation was observed, and twelve or more single cells were further observed.

FIG. 20 is a table showing the results of the microscopic observations of Example 1 and Comparative Example 1. As shown in FIG. 20, in Example 1, many single cells were observed in the liquid discharged into the centrifuge tube, and in Comparative Example 1, many single cells were observed among the cells captured by the filter.

In Example 1, since the liquid permeability was improved due to the irregular vibration of the filtration and collection device 1A during pouring of the liquid, single cells efficiently passed and dropped from the filter, and more liquid was discharged into the centrifuge tube as compared with Comparative Example 1.

In addition, in Example 1, due to the irregular vibration of the filtration and collection device 1A, the single cells attached to the filter could pass through the filter and fall into the centrifuge tube. As a result, in the liquid discharged into the centrifuge tube, more single cells could be observed in Example 1 than in Comparative Example 1.

On the other hand, as a result of observing the cells captured by the filter, in Comparative Example 1, many single cells were observed. In Comparative Example 1, it shows that the single cells remained attached to the filter base portion 14 of the filter illustrated in FIG. 6 because the filtration and collection device 101A remained on the centrifuge tube without vibration during pouring of the liquid.

From the above evaluation, it was found that, as in the filtration and collection device 1A of Example 1, irregular vibration occurs during pouring of the liquid, so that the cells can be efficiently separated.

Although the present disclosure is fully described in connection with preferred embodiments with reference to the accompanying drawings, various variations and modifications are obvious to those skilled in the art. It should be understood that such variations and modifications are included therein, as long as they do not deviate from the scope of the invention according to the appended claims.

The filtration and collection device of the present disclosure is useful for collecting biological substances in a fluid with a high collection rate, and is effectively applied to the regenerative medicine industry, the food industry, and the like.

In general, the description of the aspects disclosed should be considered as being illustrative in all respects and not being restrictive. The scope of the present invention is shown by the claims rather than by the above description, and is intended to include meanings equivalent to the claims and all changes in the scope. While preferred aspects of the invention have been described above, it is to be understood that variations and modifications will be apparent to those skilled in the art without departing from the scope and spirit of the invention.

DESCRIPTION OF REFERENCE SYMBOLS

1A, 1B, 1C, 1D FILTRATION AND COLLECTION DEVICE

10 FILTER
20 HOLDER
20*a* INLET PORT
20*b* DISCHARGE PORT
20*c* FLOW PATH
21 FIRST HOLDER
21*a* GROOVE PORTION
22 SECOND HOLDER
23 24 25 26 27 GRIP SECTION
23*a*, 24*a*, 25*a*, 26*a*, 27*a* INSERTION PORTION
23*b*, 24*b*, 25*b*, 26*b*, 27*b* NOTCH PORTION
101A FILTRATION AND COLLECTION DEVICE
110 FILTER
120 HOLDER
120*c* FLOW PATH
121 FIRST HOLDER
121*a* GRIP SECTION
122 SECOND HOLDER

The invention claimed is:

1. A filtration device comprising:
a holder including:
an inlet port configured to receive a liquid,
a discharge port configured to discharge the liquid,
a flow path through which the inlet port and the discharge port communicate, and
a groove portion formed on an outer periphery of the holder;
a filter disposed in the flow path of the holder and including a plurality of through-holes; and
a grip section including an insertion portion that is inserted into the groove portion,
wherein a gap is formed between the groove portion and the insertion portion;
wherein a thickness of the groove portion is greater than a thickness of an end of the insertion portion, and a distance between an edge of the insertion portion and a bottom of the groove portion is greater than zero, and
wherein the grip section is configured to independently and individually rotate about the holder and is formed in a flat plate shape and is stacked in a thickness direction.

2. The filtration device according to claim 1, wherein the holder further includes:
a first holder including a tubular shape and the groove portion, and
a second holder configured to be fitted into the first holder, and
wherein the filter is held by the first holder and the second holder.

3. The filtration device according to claim 1, wherein the insertion portion is formed with a plurality of notch portions.

4. The filtration device according to claim 3, wherein the plurality of notch portions are provided at equal distances.

5. The filtration device according to claim 1, wherein the grip section and has a first surface, and one or a plurality of convex portions are formed on the first surface.

6. The filtration device according to claim 1, wherein the filter includes at least one of a metal or a metal oxide.

7. The filtration device according to claim 1, wherein the discharge port is in communication with a centrifuge tube.

8. The filtration device according to claim 1, wherein the plurality of through-holes are a rectangle shape in which a length of one side in a radial direction of the filter is longer than a length of one side in a thickness direction of the filter.

9. The filtration device according to claim 1, wherein a width of the groove portion is 1.1 times or more but less than 2 times a thickness of the grip section.

10. The filtration device according to claim 1, wherein the groove portion formed on the outer periphery of the holder is annular in shape.

11. The filtration device according to claim 1, wherein less than an entire circumference of the grip section comes into contact with the holder.

12. A filtration device comprising:

a tube including an inlet port and an outlet port;

a flow path through which the inlet port and the outlet port communicate;

a filter disposed in the flow path of the tube;

an indentation formed on an outer periphery of the tube;

a plate including an insertion portion that is configured to engage with the indentation of the tube, and a void formed between the indentation and the insertion portion;

wherein a thickness of the indentation is greater than a thickness of an end of the insertion portion, and a distance between an edge of the insertion portion and a bottom of the indentation is greater than zero, and wherein the plate is configured to independently and individually rotate about the tube and is formed in a flat plate shape and is stacked in a thickness direction.

13. The filtration device according to claim 12, wherein the tube further includes:

a first tube including a tubular shape and the indentation, and a second tube configured to be fitted into the first tube in a vertical direction, and wherein the filter is held by the first tube and the second tube.

14. The filtration device according to claim 12, wherein the insertion portion is formed with a plurality of notch portions.

15. The filtration device according to claim 14, wherein the plurality of notch portions are provided at equal distances.

16. The filtration device according to claim 12, wherein the plate is formed in a flat shape and has a first surface, and one or a plurality of convex portions are formed on the first surface.

17. The filtration device according to claim 12, wherein the filter includes at least one of a metal or a metal oxide.

18. The filtration device according to claim 12, wherein the outlet port is in communication with a centrifuge tube.

19. The filtration device according to claim 12, wherein the filter includes a plurality of through-holes in a rectangle shape in which a length of one side in a radial direction of the filter is longer than a length of one side in a thickness direction of the filter.

20. The filtration device according to claim 12, wherein the plate has a first side and a second side, and further includes an opening perpendicular to the first side and second side.

* * * * *